United States Patent [19]

Joran

[11] Patent Number: 5,268,423
[45] Date of Patent: Dec. 7, 1993

[54] METHOD FOR PREPARATION OF PEPTIDE SYNTHESIS RESINS AND PEPTIDE SYNTHESIS RESINS

[75] Inventor: Alvin D. Joran, New York, N.Y.

[73] Assignee: New York University, New York, N.Y.

[21] Appl. No.: 843,115

[22] Filed: Feb. 28, 1992

[51] Int. Cl.$^5$ .................. C08F 283/00; C08G 14/00; C08G 16/00; C08L 61/00

[52] U.S. Cl. .................. 525/54.11; 530/333; 530/334; 530/335; 530/337

[58] Field of Search .................. 525/54.11, 471; 530/333, 334, 335, 337; 528/212, 218, 219

[56] References Cited

U.S. PATENT DOCUMENTS

| | | | |
|---|---|---|---|
| 1,991,743 | 2/1935 | Groggins | 568/319 |
| 2,468,762 | 5/1949 | Kosak | 568/319 |
| 3,700,609 | 10/1972 | Treagear et al. | 525/53 |
| 3,927,133 | 12/1975 | Satomura | 585/437 |
| 4,266,066 | 5/1981 | Spielmann et al. | 549/64 |
| 4,304,941 | 12/1981 | Lee et al. | 568/322 |
| 4,511,478 | 8/1985 | Nowinski et al. | 210/691 |
| 4,623,484 | 11/1986 | Carpino et al. | 525/54.11 |
| 4,743,669 | 5/1988 | Young | 522/200 |
| 4,758,623 | 7/1988 | Leznoff | 525/54.11 |
| 4,762,881 | 8/1988 | Kauer | 525/54.11 |
| 4,786,684 | 11/1988 | Glass | 525/54.11 |
| 4,859,736 | 8/1989 | Rink | 525/54.11 |
| 5,004,781 | 4/1991 | Rink | 525/54.11 |

*Primary Examiner*—Nathan M. Nutter
*Attorney, Agent, or Firm*—Browdy and Neimark

[57] ABSTRACT

A solid phase resin useful as a support for peptide synthesis is synthesized stepwise from a solid phase polymer by reacting a solid phase phenyl ether resin with an alkoxy benzoyl halide to form a solid phase having (alkoxybenzoyl)phenoxymethyl groups bound thereto. The hydroxy group of the benzoyl moiety may be converted to a free amine by reacting with an ammonium salt of a carboxylic acid and then hydrolyzing with alkali. Novel resins produced by this method include those in which the solid phase phenyl ether resin is a resin having alkyl phenyl moieties linked to alkoxy phenyl groups by an ether linkage.

19 Claims, No Drawings

SEQUENCE LISTING (1) GENERAL INFORMATION:
  (i) APPLICANT: JORAN, Alvin
  (ii) TITLE OF INVENTION: METHOD FOR PREPARATION OF PEPTIDE SYNTHESIS RESINS AND NOVEL PEPTIDE SYNTHESIS RESINS
  (iii) NUMBER OF SEQUENCES: 1
  (iv) CORRESPONDENCE ADDRESS:
    (A) ADDRESSEE: BROWDY AND NEIMARK
    (B) STREET: 419 Seventh Street, N.W.
    (C) CITY: Washington
    (D) STATE: DC
    (E) COUNTRY: USA
    (F) ZIP: 20004
  (v) COMPUTER READABLE FORM:
    (A) MEDIUM TYPE: Floppy disk
    (B) COMPUTER: IBM PC compatible
    (C) OPERATING SYSTEM: PC-DOS/MS-DOS
    (D) SOFTWARE: PatentIn Release #1.0, Version #1.25
  (vi) CURRENT APPLICATION DATA:
    (A) APPLICATION NUMBER:
    (B) FILING DATE:
    (C) CLASSIFICATION:
  (viii) ATTORNEY/AGENT INFORMATION:
    (A) NAME: BROWDY, ROGER L
    (B) REGISTRATION NUMBER: 25,618
    (C) REFERENCE/DOCKET NUMBER: JORAN2
  (ix) TELECOMMUNICATION INFORMATION:
    (A) TELEPHONE: 202-628-5197
    (B) TELEFAX: 202-737-3528
    (C) TELEX: 248633
(2) INFORMATION FOR SEQ ID NO:1:
  (i) SEQUENCE CHARACTERISTICS:
    (A) LENGTH: 4 amino acids
    (B) TYPE: amino acid
    (C) STRANDEDNESS: single
    (D) TOPOLOGY:linear
  (ii) MOLECULE TYPE: peptide
  (iii) HYPOTHETICAL: YES
  (xi) SEQUENCE DESCRIPTION: SEQ ID NO:1:
    Ala Pro Gly Ala
    1

METHOD FOR PREPARATION OF PEPTIDE SYNTHESIS RESINS AND PEPTIDE SYNTHESIS RESINS

FIELD OF THE INVENTION

The present invention relates to a method for the synthesis of certain solid phase supports useful in the synthesis of peptides as well as to novel peptide synthesis resins.

BACKGROUND TO THE INVENTION

Solid-phase synthesis protocols as described by Merrifield are well-known in the art for synthesizing peptides. A number of different resin supports have been adopted as standards in the field. Besides the original chloromethylated polystyrene of Merrifield, benzhydrylamine type resins have been widely used to prepare peptide amides (Stewart, *Solid Phase Peptide Synthesis*, Pierce Chemical Co., Rockford, IL (1984), Pietta et al, *J. Chem. Soc. D.*:650-651 (1970); Orlowski et al, *J. Org. Chem.*, 50:3701-5 (1976); Matsueda et al, *Peptides*, 2:45-50 (1981) and Tam, *J. Org. Chem.*, 50:5291-8 (1985)). These solid phases are acid labile (Albericio et al, *Int. J. Peptide Research*. 30:206-216 (1987)).

In recent years acid labile resins using a trialkoxydiphenyl-methylester moiety have become popular due to their ease of use for peptide synthesis with FMOC protected amino acids (Rink, *Tetrahedron Letters*, 28:3787-90 (1987); U.S. Pat. No. 4,859,736; and U.S. Pat. No. 5,004,781). The peptide is eventually released by cleavage with trifluoroacetic acid. This resin which is used to attach blocked amino acids for the purposes of peptide synthesis of peptides, has the following structure:

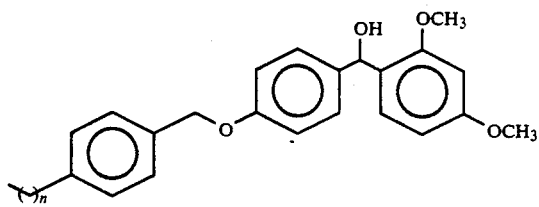

This structure is part of an insoluble polymer which will permit easy separation from liquid reactants by simple physical separations such as filtration, centrifugation, sedimentation and decanting, etc.

Rink synthesized the compound by reacting resorcinol diether with p-hydroxybenzoyl chloride in the presence of the Lewis acid aluminum chloride to give 2,4-dimethyl-4'hydroxybenzophenone. This product was suspended in ethanol and cesium hydroxide monohydrate wa added. After being allowed to react, the reaction product was lyophilized. This material was then reacted with chloromethyl-polystyrene-1% divinylbenzene, dried and suspended in pyridine three times, dried and dissolved in DMF. The ketone formed was reduced and used for peptide synthesis. The method for preparing this resin uses cesium salts and involves several chemical purification steps which are time consuming and expensive.

Using the solid phase technique during peptide synthesis has become a standard for peptide synthesis as is discussed in the Rink patents (U.S. Pat. Nos. 4,859,736 and 5,004,781), the contents of which are hereby incorporated by reference. However, the use of multistep solid phase techniques to synthesize the Rink-type solid phase itself, prior to reaction to form a peptide or ester bond, has not been achieved prior to the present invention described herein.

SUMMARY OF THE INVENTION

The present invention relates to new methods for preparing solid phase substrates for peptide synthesis and to new substrates produced by this method. The process is performed where one reactant is always in a solid phase. This permits ease of separation of the products without extensive purification. Furthermore, no purification of intermediates is required.

Accordingly, it is an object of the present invention to prepare solid phase resins for peptide synthesis without expensive reagents or extensive purifications and processing.

A further object of the present invention is to prepare a suitable solid phase substrate economically from relatively inexpensive reactants.

Another object of the present invention is to convert a substituted diaryl methyl ketone to a corresponding substituted diaryl aminomethyl group through the use of reductive amination.

Still another object of the invention is the acid catalyzed acylation of a phenyl ether. This may be done in a manner so that substantially para substitutions are made.

Yet another object of the present invention is to provide novel peptide synthesis support resins.

Is is still a further object of the present invention to provide a novel peptide synthesis support resin which is less expensive and easier to make than the Rink resin but which performs at least as well.

DETAILED DESCRIPTION OF PREFERRED EMBODIMENTS

Multi-step synthesis of peptides on a solid phase using the so-called Merrifield synthesis is well known. However, the use of a solid phase in the preparation of Rink-type solid support for peptide synthesis has not been achieved prior to the present invention. By starting with a solid phase, one can perform many synthesis steps to form the desired solid support for peptide synthesis without extensive chemical purification steps. As with peptide synthesis itself, the product at each step may be separated easily by filtration, centrifugation or sedimentation and washing. Magnetically responsive materials may be attached to the solid polymer to facilitate easy separation. This ease of separation permits straightforward purification without extensive and expensive methods. Suitable insoluble polymers include almost all resins having phenyl groups in or attached to its skeleton. Other polymers may also be used if they can be derivatized in accordance with the general techniques of the present invention. Of the other polymers, particularly preferred are those having or capable of being derivatized to have halomethyl moieties attached to a phenyl group.

The improved synthesis of the amine or hydroxy resin proceeds as shown in the following reaction schemes. A solid phase material has been derivatized to have a halo lower alkyl moiety. Halomethylated phenyl containing polymer or copolymer (1) (commercially sold under names such as "Merrifield resin") is reacted with compound (2) to yield an optionally substituted phenoxymethylphenyl resin (3) as shown in the following reaction (I):

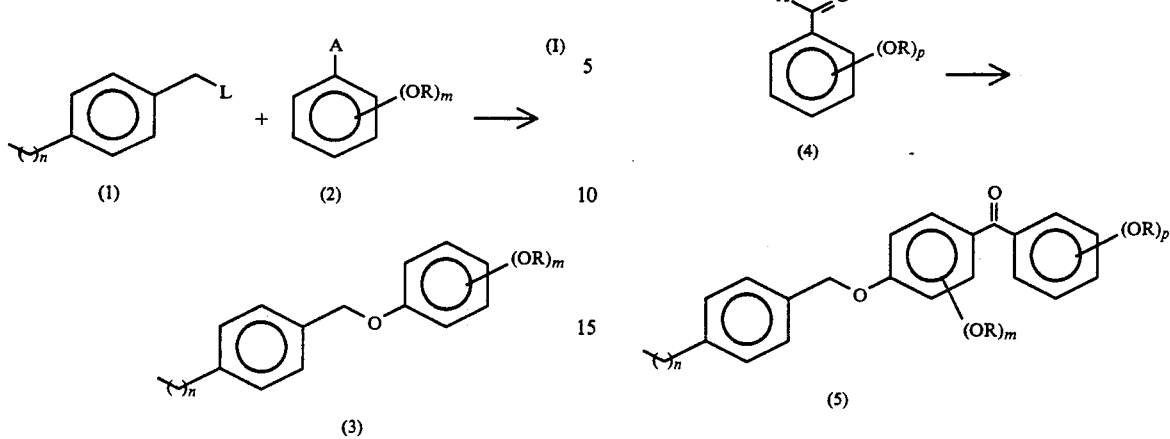

where L is a leaving group such as a halide or OH, A is OH, —ONa or —SNa, and R is an alkyl or aryl group, preferably lower alkyl and carboxylic aryl, most preferably phenyl, and m is 0–4. Roughly equimolar portions of the resin (1) and compound (2) are mixed in an organic solvent and heated until the reaction is complete. As with all of the steps in the reaction, agitation encourages contact between the fluid and resin particles to aid in the speed and completion of the reaction. The solid resin is separated from the mixture by filtration, washed with organic solvents and dried.

The next step in the procedure is the acid catalyzed acylation of the benzyl phenyl ether with an alkoxy substituted acetyl halide (4) in the presence of a Lewis acid as shown in the following reaction (II):

where R is as defined above and preferably a straight chain or branched lower alkyl, X is a halide and p is 0.5, m+p being at least 2. An excess of alkoxybenzoyl halide (4) is added and an excess of a Lewis acid is added slowly while mixing. The reaction mixture is allowed to react until complete. The solid resin product is separated, washed with organic and aqueous solvents and dried, resulting in a diaryl ketone (5).

While any Lewis acid may be used, zinc halide or aluminum halide are preferred. The chloride is the preferred halide for use in both reactions.

The ketone (5) may be reduced to an alcohol or reductively aminated by any of several reactions or series of reactions depending on whether one wishes the hydroxy or the amine form of the resin. Reduction to the hydroxy form may be done in a manner known per se to reduce ketones to alcohols. For example, such reduction may take place in the presence of alkali metal boro- or aluminum hydrides where the alkali metal is sodium, potassium, or lithium in an inert organic solvent. An example is shown below in reaction (III):

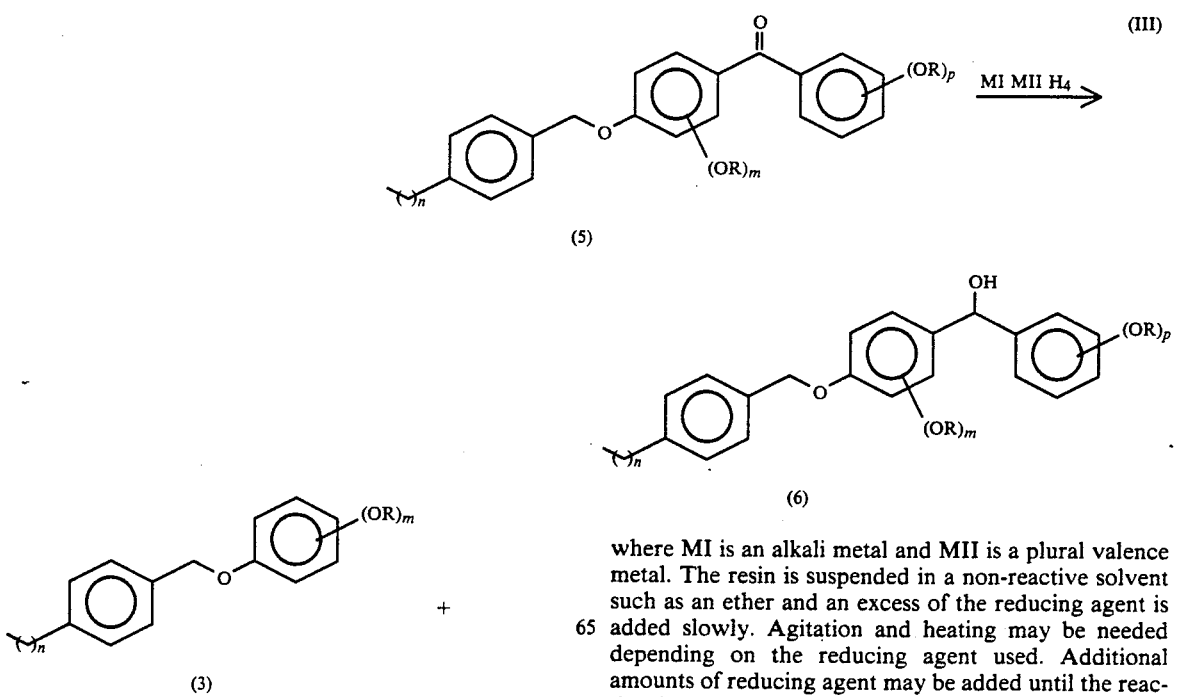

where MI is an alkali metal and MII is a plural valence metal. The resin is suspended in a non-reactive solvent such as an ether and an excess of the reducing agent is added slowly. Agitation and heating may be needed depending on the reducing agent used. Additional amounts of reducing agent may be added until the reaction is complete. Excess reducing agent is inactivated by adding a great excess of a ketone such as acetone. The resin (6) is separated by filtration from the mixture, washed and dried.

The hydroxy on this resin may be converted to an amine by reacting it with a carbamate amide compound, especially a substituted ethylcarbamate amide and an organic acid catalyst followed by cleavage of the amino-protecting group with alkali.

The β-substituted ethylcarbamate and a strong acid are added to the resin suspended in an inert organic solvent and the reaction is allowed to continue for a few hours until the reaction is completed. The resulting resin is separated, washed and dried. The amino-protecting group is removed by adding the resulting resin to an organic solvent and adding a base, preferably an organic base to yield the shown product.

The ketone resin may be converted to the amine form by reductive amination. In accordance with a preferred embodiment of the present invention, the ketone resin is reductively aminated with an ammonium salt of a carboxylic acid such as formate or other carboxylic acid and then the amine generated by cleavage with alkali. The reaction is shown below in reaction (IV):

which is obtained when compound (2) is:

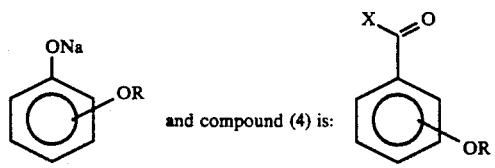

and compound (4) is:

While the OR groups can be at any position on compounds (2) and (4) the most preferred process is that where OR is meta-OMe in compound (2) and para-OMe in compound (6) to form:

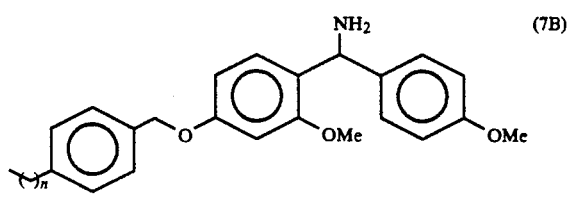

(7B)

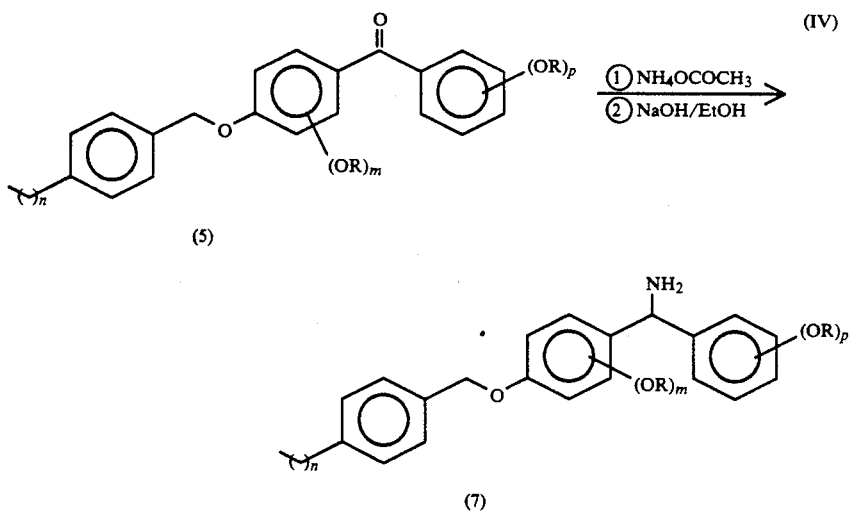

(IV)

The resin (6) is suspended in molar excess of ammonium formate and refluxed at high temperatures for about 24 hours until the reaction has occurred. After cooling, the mixture is diluted; the resin is separated, washed in organic and aqueous solvents, and dried. The resulting resin is added to an ethanolic 5N NaOH solution and refluxed until the final product (7) shown above is produced. The resin is separated from the mixture, washed with aqueous and organic solutions and dried to yield the shown product.

To produce the Rink resin, the compound (2) is phenol and compound (4) is 2,4-dialkoxyphenyl acetyl halide. A preferred alternative to the Rink resin which may be made by the process of the present invention is:

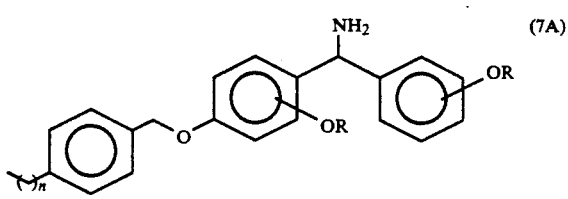

(7A)

The preferred novel compounds 7A and particularly compound 7B can easily and inexpensively be made by the process of the present invention. The starting materials for the production of resin 7B are meta-cresol and anisoyl chloride, which are readily available and inexpensive. While such resins can commercially be made by a generalized Rink procedure, such a method would suffer from several drawbacks, including the need to isolate and purify intermediates and the lack of specificity expected for the initial step, i.e., the reaction of 3-methoxyphenol with 4-methoxybenzoyl chloride in the presence of a Lewis acid. The similar electronic activation at all ortho/para positions makes them about equal in Friedel-Crafts acylation reactivity, leading to a highly impure product mixture. Because of steric hindrance, several of these regioisomers are unreactive in the acylation. The improved method of the present invention transcends this problem since the steric restriction imposed by the resin surface curtails formation of other isomers, making the product more homogeneous.

A key step in the reaction scheme of the present invention is the acid catalyzed Friedel-Crafts acylation of a benzyl phenyl ether. On elementary grounds this step is not expected to be clean mechanistically because of the potential for benzylic cation formation. Indeed, phenyl ethers are normally cleaved using Lewis acids. See Olah, *Friedel-Crafts and Related Reactions,* Vol. IV, Interscience, p. 1-109 (1965) and Palmer et al, *J. Chem Soc. B* 7: 742-44 (1968). However, excellent selectivity for the diaryl methylketone is unexpectedly obtained in the process of the present invention. While applicant does not wish to be bound by any particular theory, the observed chemoselectivity indicates that the latent cations may be hindered from further irreversible processes by the steric bulk of the resin surface, perhaps minimizing the extent of solvent or nucleophile participation. Alternatively, acylation ma be favored kinetically since the phenoxy benzene ring is more accessible and is electronically more activated towards electrophilic aromatic substitution processes. In addition, the oxygen of the carbonyl, being more polarized, might form a more stable complex with the Friedel Crafts acylation catalyst, curtailing competitive Lewis acid-base complexation. In any event the success of this step could not have been predicted from the prior art using non-immobilized reactants. Partial methoxy cleavage may be reversed by remethylation with dimethyl sulfate solution.

Whether the alcohol or the amine is formed, an amino blocked amino acid may then be added via its carboxylic acid moiety to form an ester or peptide bond. The blocking group may be removed by means conventional in the art such as by adding a secondary amine. This yields a free amine on the growing solid phase which then may act as the reactive moiety for the next amino blocked amino acid to be added. This process may be continued until any desired peptide is synthesized.

A variety of blocking groups have been used in the past which are later cleavable by various techniques. Acid labile t-BOC (t-butyloxycarbonyl), CBZ (benzyloxycarbonyl) and BPOC (N-bi-phenylisopropyloxycarbonyl) and base labile FMOC (fluoroenylmethoxycarbonyl) or the thiol labile DTS (N-dithiasuccinoyl) have been used. These are also suitable amino-protecting groups used to ensure proper synthesis of a peptide bond in the correct position. Preferred amino acids are naturally occurring L-amino acids. D-amino acids, non-naturally occurring amino acids and numerous derivatives of amino acids may also be used when desired in the peptide. Some amino acids, for example lysine, glutamine, etc., have plural amino groups which may need to be blocked.

FMOC (fluorenylmethoxycarbonyl) has become a standard amino protecting group which allows the acid chloride to be formed by reacting FMOC-amino acid-OH with $SOCl_2$. This in turn is reactive with a free amino group of a bound amino acid. After the two amino acid derivatives form a peptide bond, the FMOC may be removed by a secondary amine. Other amino-protecting agents which can be removed in alkaline conditions include substituted and unsubstituted benzyloxycarbonyl, isonicotinyloxycarbonyl, sulphonyl, acyl moieties, and the like. Tertiary butoxycarbonyl moieties and the like are also cleavable by acid. Ethoxycarbonyl groups $\beta$-substituted with a silyl group substituted with hydrocarbons and the like are cleavable using fluoride ions.

To protect any side-chain carboxyl moieties on the amino acid being added, one may use any compound known to be suitable for protecting carboxyl groups. Among the many known possibilities, alcohols are particularly preferred to form an ester which is readily cleavable by acid or base.

One may protect the hydroxy moieties on the amino acid by standard hydroxyl protecting moieties such as 2-tetrahydropyranyl or tertiary butyl or tertiary butoxycarbonyl, etc., which are acid cleavable, in order to prevent side reactions when adding an amino acid to the hydroxy resin.

The mercapto groups of methionine, cysteine and similar amino acids may be protected by any way known to reversibly protect these moieties. Acylation and alkylation by any of a large number of compounds would be acceptable.

One would choose protecting groups based upon the amino acids being added to the peptide which would be easily removable in as few steps as needed at the end of peptide synthesis.

Alternatively, the chemical synthesis of the resin may be performed on one or more monomers prior to polymerization to form the solid phase material.

The following are non-limiting examples of preferred embodiments of the present invention.

EXAMPLE 1

Production of phenoxymethylated resin

Chloromethylcopoly(styrene-1% divinylbenzene) resin (Peninsula Labs.; 0.47 mmol Cl/g); (2.0 g; 0.94 mmol) was treated with phenol crystals (0.1 g; 1.06 mmol) in the presence of sodium methoxide (0.06 g; 1.13 mmol) in N,N-dimethylacetamide (12 mL) at 84°-87° C. for 48 hours. The reaction mixture was poured into a tared filter funnel and washed N,N-dimethylacetamide (2×50 mL), p-dioxane (2×50 mL), dichloromethane (2×50 mL), and methanol (2×50 mL). The resin was dried in a vacuum desiccator (overnight) to a constant weight (1.99 g). The IR spectrum of the resin (KBr pellet; 5% w/w) showed bands at 11117 (sharp; medium), 1686, and 1721 cm$^{-1}$. The resultant product was phenoxymethylcopoly(styrene-1% divinylbenzene).

EXAMPLE 2

Production of 4-(2',4'-dimethyoxybenzoyl) phenoxymethyl resin

Phenoxymethylcopoly(styrene-1% divinylbenzene) produced by the reaction of example 1 (1.94 g; 0.91 mmol) was suspended in 14 mL nitrobenzene for 15 minutes. A solution of 2,4-dimethoxybenzoyl chloride (0.4 g; 2.00 mmol) and aluminum chloride (0.29 g; 2.17 mmol) was added dropwise with stirring. The reaction mixture thickened and became dark brown in color. After stirring overnight at room temperature (12 hours), the mixture was filtered through a tared sintered glass filter funnel, and washed (2×25 mL) with nitrobenzene, isopropanol, water, water/methanol (1:1), methanol, dichloromethane, and methanol. The resin was dried in vacuum to a constant weight (2.17 g). The IR spectrum (KBr pellet, 5% w/w) showed bands of equal strength at 1209 and 1657.4 cm$^{-1}$, about half the intensity of the polystyrene 1602 cm$^{-1}$ band. The resulting product was 4-(2',4'-dimethoxybenzoyl)phenoxymethylcopoly(styrene-1% divinylbenzene).

EXAMPLE 3

Production of 4[(2',4'-dimethoxyphenyl) (N-formyl) aminomethyl] phenoxymethyl resin The 4-(2',4'-dimethoxybenzoyl)phenoxymethylcopoly(styrene-1% divinylbenzene) produced in Example 2 (2.0) and ammonium formate (40.18 g) were placed in a round-bottom flask fitted with a Liebig condenser, and heated in an oil bath to 180°-190° C. for 20 hours. After cooling to room temperature, water was added. The mixture was filtered and washed (2×50 mL) with water, absolute ethanol, dichloromethane, and methanol. The resin was dried in vacuum (1.97 g). The IR spectrum (KBr; 5% w/w) showed a band at 1670 cm$^{-1}$. The resulting product was 4[(2',4'-dimethoxyphenyl)(N-formyl)aminomethyl] phenoxymethylcopoly (styrene-1% divinylbenzene).

EXAMPLE 4

Production of 4[(2',4'-dimethoxyphenyl)aminomethyl] phenoxymethyl resin

The 4-[(2',4'-dimethoxyphenyl) (N-formyl)aminomethyl] phenoxymethylcopoly(styrene-1% divinylbenzene) produced in Example 3 (1.91 g) was suspended in 50 mL of 5N NaOH/absolute ethanol (1:2), and heated to reflux for two hours. After cooling, the reaction mixture was filtered through a tared sintered glass filter funnel and washed (2×50 mL) with absolute ethanol, water, isopropanol, dichloromethane, and methanol. The resin was suspended in diisopropylethylamine (10% in dichloromethane) for 30 minutes, washed with dichloromethane. The resulting product was 4-[(2',4'-dimethoxyphenyl)aminomethyl]phenoxymethylcopoly (styrene-1% divinylbenzene).

EXAMPLE 5

Production of glycine loaded resin

The resin produced in Example 4 was loaded with glycine as the C-terminal amino acid by reaction with N-FMOC-glycine using one equivalent N,N'-dicyclohexylaminocarbodiimide (DCC) and 10% diisopropylethylamine (DIEA) in dichloromethane (DCM). The reaction mixture was shaken at room temperature until no free amino groups remained, according to the Kaiser test (Kaiser et al, *Analytical Biochemistry*, 34: 595 (1970)) performed on an aliquot of withdrawn resin (about 24 hours). A substitution level of 0.23 mmol/g was obtained by cleavage of the FMOC group in 50% piperidine/DCM, and determining the optical density of the liberated fluorene chromophore.

The amine resin prepared in accordance with this example possesses IR spectral characteristics identical to commercial resin prepared by the method of Rink. Several peptides, including [Lys$^8$]vasopressin and the tetrapeptide Ac-Ala-Pro-Gly-Ala-OH (Seq. Id. No. 1) have been prepared using the resin of the present invention, purified, and characterized (by amino acid analysis, mass spectrometry, and high performance liquid chromatography), confirming that the amine resin prepared by this method behaves in a similar manner to samples prepared by the original route in terms of yield and purity.

EXAMPLE 6

Production of 3-Methoxyphenoxymethylcopoly(styrene-1% divinylbenzene)

Chloromethyl (Merrifield) resin (0.47 mmol/g; 2.65 mmol) was suspended in N,N-dimethyl formamide (25 ml) and treated with 3-methoxyphenol (3.33g; 26.8 mmol) in the presence of sodium hydride (56.2% oil suspension; 1.14 g; 84.5 mmol). The reaction mixture was heated, using an oil bath at 80° C. for 48 hours. The reaction mixture was cooled to room temperature and filtered. The resin was washed with N,N-dimethyl formamide, isopropanol, ethanol/water (1:1), ethanol, dichloromethane, and ethanol (4×50 mL of each), and dried to a constant weight (5.70 g). IR (KBr): 1721, 1686, 1117 cm$^{-1}$.

EXAMPLE 7

Production of 4-(4-Methoxybenzoyl)-3-methoxyphenoxymethylcopoly(styrene-1% divinylbenzene)

3-Methoxyphenoxymethylcopoly(styrene-1% divinylbenzene) (1.00 g) was suspended in nitrobenzene (10 mL), and the reaction vessel was placed in an ice bath. To this suspension was added p-methoxybenzoyl chloride (1.01 g; 5.86 mmol) and aluminum chloride (2.36 g; 17.7 mmol). The reaction mixture was stirred at 0°-5° for 2 hours, and then filtered. The resin was washed with nitrobenzene, isopropanol, ethanol/water (1:1), ethanol, dichloromethane, and ethanol (4×50 mL of each), and dried to a constant weight (1.10 g). IR (KBr): 1735, 1653, 1157 cm$^{-1}$.

EXAMPLE 8

Production of 4-[(4'-Methoxyphenyl)aminomethyl-N-formylaminomethyl]-3-methoxyphenoxymethylcopoly(styrene-1% divinylbenzene)

Ammonium formate (20.27 g) was heated to 140° C. in a 500 ml round bottom flask surmounted by a reflux condenser using an oil bath. 4-(4'-Methoxybenzoyl)-3-methoxypheoxymethylcopoly(styrene-1% divinylbenzene) (1.01 g) was added. The reaction mixture was heated at reflux (160°-170° C.) for 20 hours, cooled to room temperature, and filtered, and the resin was washed with ethanol/water (1:1, isopropanol, ethanol, dichloromethane, and ethanol (4×50 mL of each), and dried to a constant weight (0.99 g). IR (KBr): 1693, 1157 cm$^{-1}$.

EXAMPLE 9

Production of 4-[(4'-Methoxyphenyl)aminomethyl]-3-methoxyphenoxymethylcopoly(styrene-1% divinylbenzene)

4-[(4'-Methoxyphenyl)aminomethyl-N-formylaminomethyl]-3-methoxyphenoxymethylcopoly(styrene-1% divinylbenzene) (0.99 g) was suspended in a ethanolic 6M KOH (20 mL), and heated at reflux for two hours. The reaction was cooled to room temperature and filtered. The resin was washed with ethanol/water (1:1), ethanol, isopropanol, dichloromethane, 5% ethanedithiol/isopropanol, 5% diisopropylethylamine/dichloromethane, dichloromethane, and ethanol (4×50 mL of each), and dried to a constant weight (0.93 g). Kaiser test: strongly positive.

EXAMPLE 10

Production of FMOC-Gly-Resin

The amine resin was suspended in 10 mL dichloromethane, and cooled in an ice-water bath. To this suspension was added a solution of FMOC-Gly-OH (0.65 g; 2.2 mmol), diisopropylcarbodiimide (343 μL; 2.19 mmol) and hydroxybenzotriazole (0.30 g; 2.22 mmol) in dichloromethane/N,N-dimethylformamide (1:1; 7 mL). The reaction mixture was stirred in the presence of 1 mL diisopropylethyl amine for 3 hours. The resin was filtered and washed with isopropanol, ethanol, dichloromethane, and ethanol, and dried to a constant weight (0.97 g). IR (KBr): 3200(br) cm$^{-1}$.

EXAMPLE 11

Determination of the Substitution Level

A (duplicate) weighted aliquot (ca. 5 mg) of the FMOC-Gly-resin was treated with 400 μL piperidine in an equal volume of dichloromethane in a 10 mL volumetric flask at room temperature for 30 minutes. To the suspension was added 1.6 mL methanol. The volume of the mixture was brought up to 10 mL with dichloromethane. The resin beads were separated by filtering through glass wool, and the absorbance of the filtrate was measured at 301 nm. The loading of the first amino acid on the resin was determined to be 0.45 mmol/g ($\epsilon_{301} = 7,800$).

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

---

---

What is claimed is:

1. A process for making a solid phase resin useful in the production of a support for peptide synthesis, comprising:

reacting, in the presence of a Lewis acid, a solid phase phenyl ether resin of the formula:

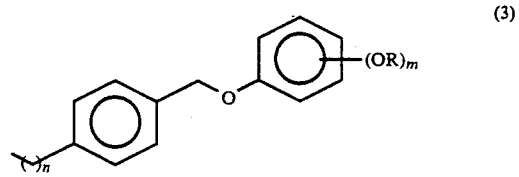

where R is an alkyl or aryl group, m is 0-4 and represents a polymeric support, with a benzoyl halide of the formula:

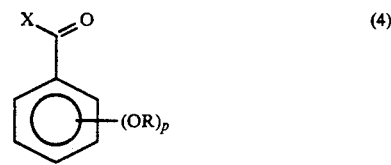

where R is as defined above, X is a halide, and p is 0-5, m+p being at least 2, to form a resin of the formula:

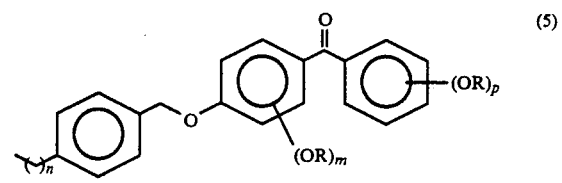

2. A process in accordance with claim 1 wherein said Lewis acid is a metal chloride.

3. A process in accordance with claim 1 wherein said polymeric support is a copolymer of styrene and divinylbenzene.

4. A process in accordance with claim 1, further including the step of reacting said resin of the formula:

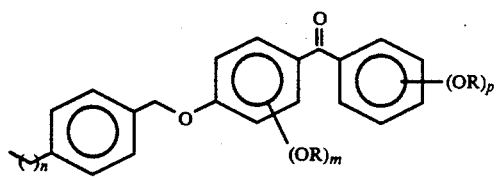

with an ammonium salt of a carboxylic acid to generate a secondary formyl amine and then hydrolyzing the secondary formyl amine with alkali to generate a free amine of the formula:

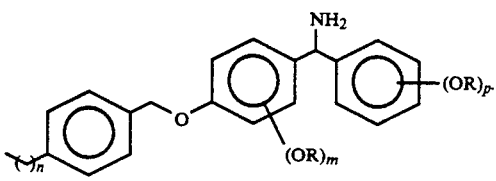

5. A process in accordance with claim 1, further including the step of reductively aminating said resin of formula (5) to generate a free amino of the formula:

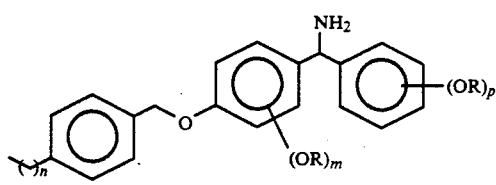

6. A process in accordance with claim 5, wherein R is a straight chain or branched lower alkyl, m is 1 and p is 1.

7. A process in accordance with claim 6, wherein R is a straight chain or branched lower alkyl, m is 0 and p is 2.

8. A process in accordance with claim 5, wherein R is a straight chain or branched lower alkyl, m is 0 and p is 2.

9. A process in accordance with claim 5, further including the step of reacting the amine with a carboxylic acid moiety of an amino-blocked amino acid.

10. A process in accordance with claim 9, further including the step of removing the blocking group from the amino end of said amino-blocked amino acid and reacting said amino end with a carboxylic acid moiety of an additional amino-blocked amino acid.

11. A process in accordance with claim 1, further including the step of reducing said resin of formula (5) to an alcohol of the formula:

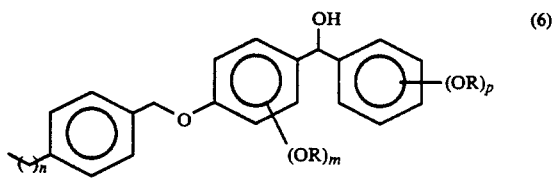

12. A process in accordance with claim 11 wherein said benzoyl halide is 2',4'-dimethoxybenzoyl chloride and m=0.

13. A process in accordance with claim 11, wherein R is a straight chain or branched lower alkyl, m is 1 and p is 1.

14. A process in accordance with claim 1, wherein R is a straight chain or branched lower alkyl or a carboxylic aryl.

15. A process in accordance with claim 14, wherein R is methyl or phenyl.

16. A solid phase resin useful as a support for peptide synthesis, having the formula:

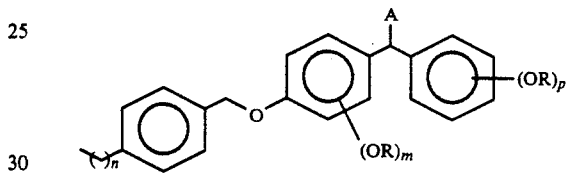

wherein R is an alkyl or aryl group, m is 1–4 and p is 1–5, A is OH or NH and

represents a polymeric support.

17. A solid phase resin in accordance with claim 16 wherein R is a straight chain or branched lower alkyl or a carboxylic aryl.

18. A solid phase resin in accordance with claim 17, wherein m=1 and p=1.

19. A solid phase resin in accordance with claim 18 of the formula:

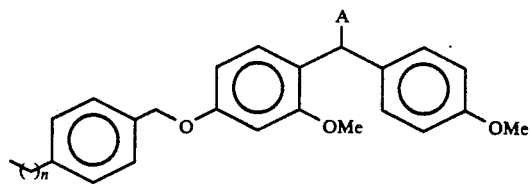

wherein Me is methyl.

* * * * *